United States Patent [19]

Iida et al.

[11] Patent Number: 4,803,213

[45] Date of Patent: Feb. 7, 1989

[54] METHOD FOR PRODUCTION OF STABLE NICORANDIL PREPARATION

[75] Inventors: Yoshimitsu Iida; Takashi Terazono, both of Saitama; Shuji Sumida, Tokyo, all of Japan

[73] Assignee: Chugai Seiyaku Kabushiki Kaisha, Tokyo, Japan

[21] Appl. No.: 147,129

[22] Filed: Jan. 21, 1988

Related U.S. Application Data

[63] Continuation of Ser. No. 805,290, Dec. 5, 1985, abandoned.

[30] Foreign Application Priority Data

Dec. 17, 1984 [JP] Japan .................................. 59-265888
Jun. 26, 1985 [JP] Japan .................................. 60-213277
Jul. 8, 1985 [JP] Japan .................................. 60-149688

[51] Int. Cl.$^4$ .............................................. A61K 31/44
[52] U.S. Cl. ................................... 514/355; 514/960; 514/970
[58] Field of Search ................. 574/355, 356, 970, 960

[56] References Cited

U.S. PATENT DOCUMENTS

| | | | |
|---|---|---|---|
| 3,168,438 | 2/1965 | Halpern | 514/356 |
| 3,332,848 | 7/1967 | Clifton | 514/355 |
| 3,577,491 | 2/1971 | Cox. | |
| 4,200,640 | 8/1980 | Nagano et al. | |
| 4,323,577 | 4/1982 | Ohkuma et al. | 514/970 |
| 4,382,091 | 5/1983 | Benjamin et al. | 514/970 |
| 4,490,377 | 12/1984 | Chowhan | 514/970 |
| 4,565,824 | 1/1986 | Wehinger et al. | 514/356 |

FOREIGN PATENT DOCUMENTS

| | | |
|---|---|---|
| 0045238 | 8/1982 | European Pat. Off. . |
| 2714713 | 4/1977 | Fed. Rep. of Germany . |

OTHER PUBLICATIONS

Chem. Abst. 88:22652h (1978)–Nagano et al.
Chem. Abst. 99: 58932v (1983)–Chugai Pharm.

Primary Examiner—Douglas W. Robinson
Attorney, Agent, or Firm—Browdy and Neimark

[57] ABSTRACT

A method for producing a stable pharmaceutical preparation containing nicorandil as an active ingredient is disclosed. The stable preparation is produced by mixing nicorandil, one or more finely comminuted sugars, and/or one or more powdery organic acids.

Nicorandil which is useful as a curative for various types of angina pectoris is not stable against the compressive pressure exerted by punching operations in tabelt making or against moisture.

The preparation of nicorandil manufactured by this invention is very stable and useful in clinical applications.

5 Claims, 2 Drawing Sheets

METHOD FOR PRODUCTION OF STABLE NICORANDIL PREPARATION

This application is a continuation of application Ser. No. 805,290, filed Dec. 5, 1985 now abandoned.

BACKGROUND OF THE INVENTION

The present invention relates to a method for producing a stable preparation of nicorandil [N-(2-hydroxyethyl)nicotinamide nitrate (ester)] that will be very useful as a drug. More particularly, the present invention relates to a method for producing a stable nicorandil preparation containing a finely divided sugar and/or a powdery organic acid as an excipient.

The stability of drugs is dependent on various factors such as temperature, humidity, light and oxygen. Many proposals have heretofore been made with a view to producing stable drug preparations.

Nicorandil which is to be produced in a stable form by the present invention has coronary vasodilative and coronary vasoconstriction suppressing actions and is useful as a curative for various types of angina pectoris while causing minimum effects on the dynamics of cardiovascular circulation and on cardiac functions (see Japanese Patent Publication No. 17463/1983 and Unexamined Published Japanese Patent Application No. 9323/1978).

However, nicorandil preparations are not stable against the compressive pressure exerted by punching operations in tablet making and will experience a time-dependent decrease in the amount of the active principle. Conventional practice employed to avoid this problem is to coat the nicorandil crystal with stearyl alcohol or other coating materials (Unexamined Published Japanese Patent Application No. 145659/1982).

Nicorandil preparations which are fairly stable in the dry state but instable in humid conditions and must be produced and stored with special care being taken to avoid direct contact with moisture by, for example, wrapping in a completely moistureproof package which, however, is quite expensive.

SUMMARY OF THE INVENTION

The present inventors, therefore, made various studies in order to develop a method for producing a nicorandil preparation that is stable against the pressure of compression and humidity. As a result, the inventors found that by using a finely divided sugar as an excipient, a significant improvement is achieved in the stability of a nicorandil preparation against compressive pressure, with its stability against moisture being also improved to some extent. The inventors also found that by using a certain type of organic acid as an excipient, the nicorandil preparation is provided with an appreciably improved stability against moisture, this being also true even when it is compressed into a tablet. It was additionally found that significant improvements could be achieved in the stability to both compressive pressure and humidity by using an excipient made of a finely divided sugar and a certain type of organic acid. The present invention has been accomplished on the basis of these findings.

Detailed Description of the Invention

Figure 1:
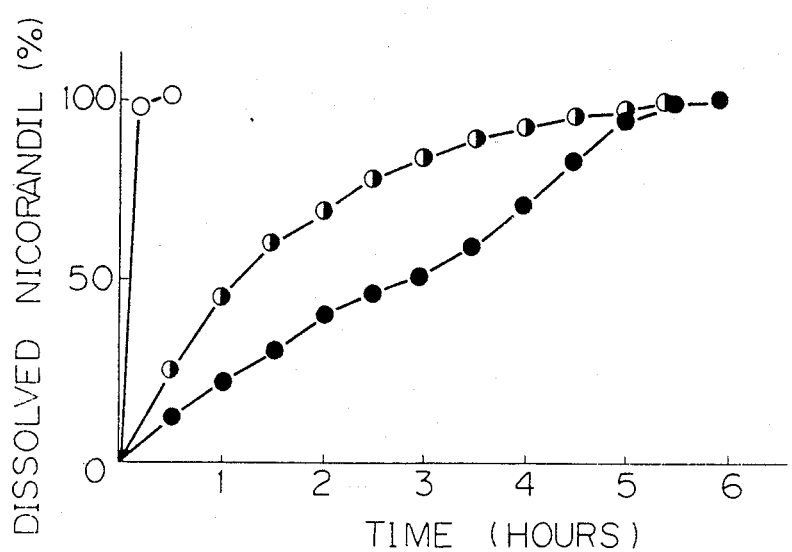
FIG. 1 is a graph showing a dissolution profile of each of the multi-layer tablet gradually releasing nicorandil prepared in Example 10 (—•—), the ordinary tablet of the Comparative Example (—•—), and the tablet gradually releasing nicorandil prepared in Example 11 (—o—).

Examples of the sugar that may be used as the excipient in the method of the present invention are mannitol, lactose, sucrose, glucose, fructose, galactose, maltose and any other sugars that are commonly used in foods and medicines. These sugars are used in a finely divided form and particularly good results are obtained when they are used as particles having an average size of no more than 10 $\mu$m. A jet mill may be used as a grinding machine. The finely divided sugar is granulated by a suitable method, for example, a wet granulation process and then blended with the active ingredient. The proportion of the sugar to be blended may be properly adjusted depending upon the amount of the active ingredient in the finally prepared tablet and the punching pressure. The intended stabilizing effect of the sugar will be obtained if its amount is within the range in which it is customarily used as an excipient for pharmaceutical preparations. The tablet produced in accordance with the present invention may contain suitable amounts of a disintegrator, binder and lubricant.

Organic acids that will exhibit particularly excellent stabilizing effects are dibasic acids such as fumaric acid, oxalic acid, salicylic acid, tartaric acid and glutaric acid. A composition consisting of nicorandil and a pharmaceutical vehicle such as an excipient, disintegrator, lubricant, colorant or binder is blended with at least one organic acid selected from the group consisting of fumaric acid, oxalic acid, salicylic acid, tartaric acid and glutaric acid, and the resulting blend is processed into a desired dosage form, such as tablet, capsule, granule or suppository, by a conventional method. The proportion of the organic acid may vary depending upon the amount of the active ingredient in the preparation and the method of its production, but the intended stabilizing effect of the organic acid will be attained by adding no less than 0.1 wt % of the total weight of the preparation.

A nicorandil preparation that is very stable against compressive pressure and moisture can be produced by using an excipient made of the finely divided sugar in combination with one or more of the aforementioned organic acids as in the manner described above.

The following examples are provided for the purpose of further illustrating the present invention but are not to be construed as limiting.

EXAMPLE 1

One part of N-(2-hydroxyethyl)nicotinamide nitrate ester (nicorandil) was intimately blended with 9 parts of a mannitol granulation prepared by a wet process from jet-milled particles (av. size, 3 $\mu$m). The blend was compressed statically into tablets (10 mm$^\phi$ and 300 mg in weight) having a hardness of ca. 10 kg as messured by an automatic hardness tester (Okada Seiko K.K.). Another group of tablets was produced by the same procedures using a non-comminuted mannitol powder. The two groups of tablets were stored under accelerated conditions (50° C. in a desiccator with a desiccant, silica gel). The results are shown in Table 1 wherein the numerals indicate the residual amount of nicorandil in the tablet as a percentage of the initial weight.

TABLE 1

| accelerated time (day) | 4 | 7 | 10 | 14 |
|---|---|---|---|---|
| sample of the invention | 98.8 | 96.5 | 93.7 | 88.3 |
| comparative sample | 96.7 | 88.3 | 80.2 | 65.0 |

EXAMPLE 2

| | |
|---|---|
| Nicorandil | 10 (mg) |
| Lactose | 89.5 |
| Calcium stearate | 0.5 |
| Total | 100.0 (mg) |

Lactose (268.5 g) that had been comminuted by a jet mill (Model FS-4 of Seishin Kigyo K.K.) into particles with an average size of 5 μm was put into a mortar and kneaded with water. The kneaded lactose was sieved through a 35 mesh screen and dried at 50° C. for 3 hours. The dried particles were classified by passage through a 35 mesh sieve to prepare a lactose granulation. Nicorandil (30 g), the lactose granulation (268.5 g) and calcium stearate (1.5 g) were mixed in a polyethylene bag.

Using a single-punch machine (Model N-20 of Okada Seiko K.K.) equipped with 7 mm$^\phi$ flat-faced punches, the mixed powder was compressed at 0.6 ton, 0.9 ton and 1.2 tons, to make tablets each weighing 100 mg.

Comparative tablets were made under the same conditions as described above except that the comminuted lactose particles (av. size, 5 μm) were replaced by non-comminuted lactose particles (av. size, 100 μm).

The two groups of tablets were put into glass bottles in the presence of a desiccant (silica gel) and screw-capped, then stored at 50° C. for 10 days. The results are shown in Table 2 wherein the tablet stability is indicated by the residual amount of nicorandil as a percentage of the initial weight.

TABLE 2

| | Residual nicorandil (%) | | |
|---|---|---|---|
| Tablet | 0.6 ton | 0.9 ton | 1.2 tons |
| sample of the invention | 92.8 | 92.5 | 91.8 |
| comparative sample | 88.4 | 83.2 | 77.2 |

EXAMPLE 3

| | |
|---|---|
| Nicorandil | 10 (mg) |
| Mannitol | 84.5 |
| Carboxymethylcellulose calcium | 5 |
| Magnesium stearate | 0.5 |
| Total | 100.0 (mg) |

Mannitol (253.5 g) that had been comminuted by a jet mill (Model FS-4 of Seishin Kigyo K.K.) into particles with an average size of 3 μm was put into a mortar and kneaded with water. The kneaded mannitol was sieved through a 35 mesh screen and dried at 50° C. for 3 hours. The dried mannitol particles were classified by passage through a 35 mesh sieve to prepare a mannitol granulation. Nicorandil (30 g), the mannitol granulation (253.5 g), carboxymethylcellulose calcium (15 g) and magnesium stearate (1.5 g) were mixed in a polyethylene bag.

Using a single-punch machine (Model N-20 of Okada Seiko K.K.) equipped with 7 mm$^\phi$ flat-faced punches, the mixed powder was compressed at 1.2 tons to make tablets each weighing 100 mg.

Comparative tablets were made under the same conditions as described above except that the comminuted mannitol particles (av. size, 3 μm) were replaced by non-comminuted mannitol particles (av. size, 50 μm).

Each of the two groups of tablets was divided into two subgroups. They were put into glass bottles and stored under accelerated conditions at 50° C. One set of subgroups was held for 10 days in the presence of a desiccant (silica gel), with the bottles screw-capped, whereas the other set of subgroups was held for 5 days at 50% R.H., with the bottles left open. The results are shown in Table 3 wherein the tablet stability is indicated by the residual amount of nicorandil as a percentage of the initial weight.

TABLE 3

| | Residual nicorandil (%) | |
|---|---|---|
| Tablet | 10 days in closed bottles with a desiccant | 5 days in open bottles at 50% R.H. |
| sample of the invention | 90.2 | 71.5 |
| comparative sample | 76.6 | 64.3 |

EXAMPLE 4

Tablet formulation (for one tablet)

| | |
|---|---|
| Nicorandil | 10 (mg) |
| Lactose | 76.5 |
| Corn starch | 10 |
| Fumaric acid | 3 |
| Magnesium stearate | 0.5 |
| Total | 100.0 (mg) |

Nicorandil (200 g), lactose (1,530 g; average particle size, 100 μm), corn starch (200 g) and a fine powder of fumaric acid (60 g; average particle size, 3 μm) were mixed in a Shinagawa mixer for 20 minutes, and for another 1 minute after addition of magnesium stearate (10 g).

The mixed powder was compressed using a single-punch machine equipped with 7 mm$^\phi$ flat-faced punches at 1 ton to produce tablets each weighing 100 mg.

Comparative tablets were made under the same conditions as above except that the fumaric acid was replaced by an equal amount of lactose particles (av. size, 100 μm).

Each of the two groups of tablets was divided into two subgroups. They were put into glass bottles and stored under accelerated conditions at 40° C. One set of subgroups was held for 3 months with the bottles screw-capped, whereas the other set of subgroups was held for 3 months at 61.5% R.H. with the bottles left open. The results are shown in Table 4 wherein the tablet stability is indicated by the residual amount of nicorandil as a percentage of the initial weight.

TABLE 4

| | Residual nicorandil (%) | |
|---|---|---|
| Tables | in closed bottles | in open bottles at 61.5% R.H. |
| sample of the invention | 98.2 | 95.1 |

TABLE 4-continued

| Tables | Residual nicorandil (%) | |
|---|---|---|
| | in closed bottles | in open bottles at 61.5% R.H. |
| comparative sample | 57.8 | 11.9 |

EXAMPLE 5

| Nicorandil | 10 (mg) |
|---|---|
| Mannitol | 44 |
| Carboxymethylcellulose calcium | 5 |
| Salicylic acid | 40 |
| Calcium stearate | 1 |
| Total | 100.0 (mg) |

Nicorandil (200 g), mannitol (880 g; average particle size, 50 μm), carboxymethylcellulose calcium (100 g), salicylic acid (800 g) and calcium stearate (20 g) were uniformly mixed in a polyethylene bag. The mixture was treated in a roller compactor and the slugs were classified by passage through a 10 mesh screen to produce granules.

The granules were filled into hard gelatin capsules (No. 3) so that each of them contained 100 mg of the granules.

Comprative capsules were prepared under the same conditions as above except that the salicylic acid was replaced by an equal amount of mannitol particles (av. size, 50 μm).

Each of the two groups of capsules was divided into two subgroups. They were put into glass bottles and stored under accelerated conditions at 40° C. One set of subgroups was held for 3 months with the bottles screw-capped in the presence of a desiccant (silica gel), whereas the other set was held for 3 months with the bottles screw-capped but in the absence of silica gel. The results are shown in Table 5 wherein the tablet stability is indicated by the residual amount of nicorandil as a percentage of the initial weight.

TABLE 5

| Tablet | Residual nicorandil (%) | |
|---|---|---|
| | with a desiccant | without desiccant |
| sample of the invention | 99.1 | 91.3 |
| comparative sample | 78.7 | 45.5 |

EXAMPLE 6

| Nicorandil | 50 (mg) |
|---|---|
| Mannitol | 920 |
| Oxalic acid | 10 |
| Corn starch | 20 |
| Total | 1,000 (mg) |

Nicorandil (100 g), mannitol (1,840 g; average particle size, 50 μm) and oxalic acid (20 g) were mixed in a blender of the vertical shift type, e.g. a Shinagawa mixer for 20 minutes, and kneaded for 10 minutes after addition of 10% corn starch paste (400 g).

The mixture was granulated in a cylinder type granulator equipped with a 1.0 mmφ occelated screen. The granules were dried in a tray dryer at 50° C. for 4 hours. The dried granules were classified by passage through a 10 mesh sieve.

Comparative granules were prepared under the same conditions as above except that the oxalic acid was replaced by an equal amount of mannitol particles (av. size, 50 μm).

Each of the two groups of granules was divided into two subgroups. They were put into glass bottles and stored under accelerated conditions at 40° C. for 3 months. The first set of subgroups was held with the bottles screwcapped, whereas the other set was held at 61.5% R.H. with the bottles left open. The results are shown in Table 6 wherein the granules' stability is indicated by the residual amount of nicorandil as a percentage of the initial weight.

TABLE 6

| Granule | Residual nicorandil (%) | |
|---|---|---|
| | in closed bottles | in open bottles at 61.5% R.H. |
| sample of the invention | 89.4 | 86.9 |
| comparative sample | 40.8 | 9.5 |

EXAMPLE 7

| Nicorandil | 10 (mg) |
|---|---|
| Mannitol | 74.5 |
| Carboxymethylcellulose calcium | 5 |
| Fumaric acid | 10 |
| Magnesium stearate | 0.5 |
| Total | 100.0 (mg) |

Mannitol (223.5 g; average particle size, 50 μm) was put into a mortar and kneaded with water. The wet mass was sieved through a 35 mesh screen and dried at 50° C. for 3 hours. The dried mannitol particles were classified by passage through a 35 mesh sieve to prepare a mannitol granulation. Nicorandil (30 g), the mannitol granulation (223.5 g), carboxymethylcellulose calcium (15 g), fumaric acid (30 g) and magnesium stearate (1.5 g) were mixed in a polyethylene bag.

Using a single-punch machine (Model N-20 of Okada Seiko K.K.) equipped with 7 mmφ flat-faced punches, the mixed powder was compressed at 1.2 tons to make tablets each weighing 100 mg.

Comparative tablets were made under the same conditions as above except that the fumaric acid was replaced by an equal amount of the mannitol granulation.

Each of the two groups of tablets was divided into two subgroups. They were put into glass bottels and stored under accelerated conditions at 50° C. The first set of subgroups was held for 10 days with the bottles screw-capped in the presence of a desiccant (silica gel), whereas the second set of subgroups was held for 5 days at 50% R.H. with the bottles left open. The results are shown in Table 7, wherein the tablet stability is indicated by the residual amount of nicorandil as a percentage of the initial weight.

TABLE 7

| Tablet | Residual nicorandil (%) | |
|---|---|---|
| | 10 days in closed bottles with a desiccant | 5 days in open bottles at 50% R.H. |
| sample of the invention | 81.9 | 82.3 |
| comparative sample | 76.6 | 64.3 |

EXAMPLE 8

| | |
|---|---|
| Nicorandil | 10 (mg) |
| Mannitol | 74.5 |
| Carboxymethylcellulose calcium | 5 |
| Fumaric acid | 10 |
| Magnesium stearate | 0.5 |
| Total | 100.0 (mg) |

Mannitol (223.5 g) which had been ground in a jet mill (Model FS-4 of Seishin Kigyo K.K.) into particles with an average size of 3 μm was put into a mortar and kneaded with water. The wet mass was sieved through a 35 mesh screen and dried at 50° C. for 3 hours. The dried mannitol particles were classified by passage through a 35 mesh screen to prepare a mannitol granulation. Nicorandil (30 g), the mannitol granulation (223.5 g), carboxymethylcellulose calcium (15 g), fumaric acid (30 g) and magnesium stearate (1.5 g) were mixed in a polyethylene bag.

Using a single-punch machine (Model N-20 of Okada Seiko K.K.) equipped with 7 mm$\phi$ flat-faced punches, the mixed powder was compressed at 1.2 tons to make tablets each weighing 100 mg.

Comparative tabelts were made under the same conditions as described above except that the comminuted mannitol particles and fumaric acid were replaced by non-comminuted mannitol particles (av. size, 50 μm) in an amount equal to the total of the two components.

Each of the two groups of tablet was diided into two subgroups. They were put into glass bottles and stored under accerlerated conditons at 50° C. One set of subgroups was held for 10 days in the presence of a desiccant (silica gel), with the bottles screw-capped, whereas the other set of subgroups was held for 5 days at 50% R.H., with the bottles left open.

The results are shown in Table 8 wherein the tablet stability is indicated by the residual amount of nicorandil as a percentage of the initial weight.

TABLE 8

| | Residual nicorandil (%) | |
|---|---|---|
| Tablet | 10 days in closed bottles with a desiccant | 5 days in open bottles at 50% R.H. |
| sample of the invention | 92.3 | 86.5 |
| comparative sample | 76.6 | 64.3 |

EXAMPLE 9

| | |
|---|---|
| Nicorandil | 10 (mg) |
| Lactose | 59 |
| Corn starch | 10 |
| Salicylic acid | 20 |
| Calcium stearate | 1 |
| Total | 100.0 (mg) |

Lactose (177 g) which had been ground in a jet mill (Model FS-4 of Seishin Kigyo K.K.) into particles with an average size of 5 μm was put into a mortar and kneaded with water. The wet mass was sieved through a 35 mesh screen and dried at 50° C. for 3 hours. The dried lactose particles were classified by passage through a 35 mesh screen to prepare a lactose granulation.

Nicorandil (30 g), the lactose granulation (177 g), corn starch (30 g), salicylic acid (60 g) and calcium stearate (3 g) were blended in a polyethylene bag.

Using a sincle-punch tablet machine (Model N-20 of Okada Seiko K.K.) equipped with 7 mm$\phi$ flat-faced punches, the mixed powder was compressed at 1.2 tons to make tablets each weighing 100 mg.

Comparative tablets were made under the same conditions as described except that the comminuted lactose particles and salicylic acid were replaced by non-comminuted lactose particles (av. size, 100 μm) in an amount equal to the total of the two components.

Each of the two groups of tablets was divided into two subgroups. They were put into glass bottles and stored under accelerated conditions at 50° C. One set of subgroups was held for 10 days in the presence of a desiccant (silica gel), with the bottles screw-capped, whereas the other set of subgtoups was held for 5 days at 50% R.H., with the bottles left open.

The results are shown in Table 9 wherein the tablet stability is indicated by the residual amount of nicorandil as a percentage of the initial weight.

TABLE 9

| | Residual nicorandil (%) | |
|---|---|---|
| Tablet | 10 days in closed bottles with a desiccant | 5 days in open bottles at 50% R.H. |
| sample of the invention | 90.7 | 87.0 |
| comparative sample | 71.3 | 59.6 |

Among the organic acids which exhibit the activity of stabilizing nicorandil, fumaric acid displays the additional properties of gradually releasing nicorandil from the tablets over a long period of time if it is used.

A prolonged release tablet may be prepared by weighing desired amounts of nicorandil and excipient and mixing them by a usual method.

A desired amount of fumaric acid within the range of more than about 10% of the total weight of the preparation provides a desirable effect of gradual release of nicorandil. To the thus prepared mixture containing nicorandil and fumaric acid, lubricants such as magnesium stearate, calcium stearate, talc, etc. were added and the mixture was compressed in a tabelt machine to form tablets.

Further, nicorandil may be formulated into troches by using sucrose, flavoring and coloring agents, etc and compressed into a predetermined shape.

In order to obtain a desired dissolution profile, nicorandil may be formulated into multi-layer tablets by laminating a layer B free from nicorandil on a layer A containing nicorandil and compressing the layers into tablets.

Alternatively, an aqueous solution or an organic solvent solution of a binder such as hydroxypropyl cellulose, hydroxypropylmethyl cellulose, corn starch paste or the like may be added to a mixed powder containing nicorandil, and the mixture may be kneaded, dried and passed through screen of desired mesh size to make granules. The granules may be filled into hard gelatin capsules to make a capsule preparation, or coated with an enteric coating material such as hydroxypropylmethyl cellulose phthalate or carboxymethylethyl cellulose to make intestinal soluble granules.

EXAMPLE 10

|  | Upper layer | Lower layer |
| --- | --- | --- |
| Nicorandil | 10 (mg) |  |
| Fumaric acid | 99.5 | 39.8 (mg) |
| Magnesium stearate | 0.5 | 0.2 |
| Total | 110.0 (mg) | 40.0 (mg) |

Nicorandil (10 g), fumaric acid (99.5 g) and magnesium stearate (0.5 g) were mixed in a polyethylene bag to prepare a mixture (Mixed powder A).

Separately, fumaric acid (39.8 g) and magnesium stearate (0.2 g) were mixed in a polyethylene bag to prepare a mixture (Mixed powder B).

Using a single-punch tablet machine equipped with 8 mm$\phi$ flat-faced punches, mixed powder A (110 mg) was fed and lightly compressed and then mixed powder B (40 mg) was fed on the compressed mixed powder A and compressed at 1.2 tons to make tablets.

COMPARATIVE EXAMPLE

| Nicorandil | 10 (mg) |
| --- | --- |
| Lactose | 94.3 |
| Crystalline cellulose | 45 |
| Magnesium stearate | 0.7 |
| Total | 150.0 (mg) |

For comparison, tablets were prepared by mixing nicorandil (10 g), lactose (94.3 g), crystalline cellulose (45 g) and magnesium stearate (0.7 g) in a polyethylene bag. By using a single-punch tablet machine equipped with 8 mm$\phi$ flat-faced punchens, the mixed powder was compressed at 1.2 tons to make ordinary tablets each weighing 150 mg.

Figure 2:
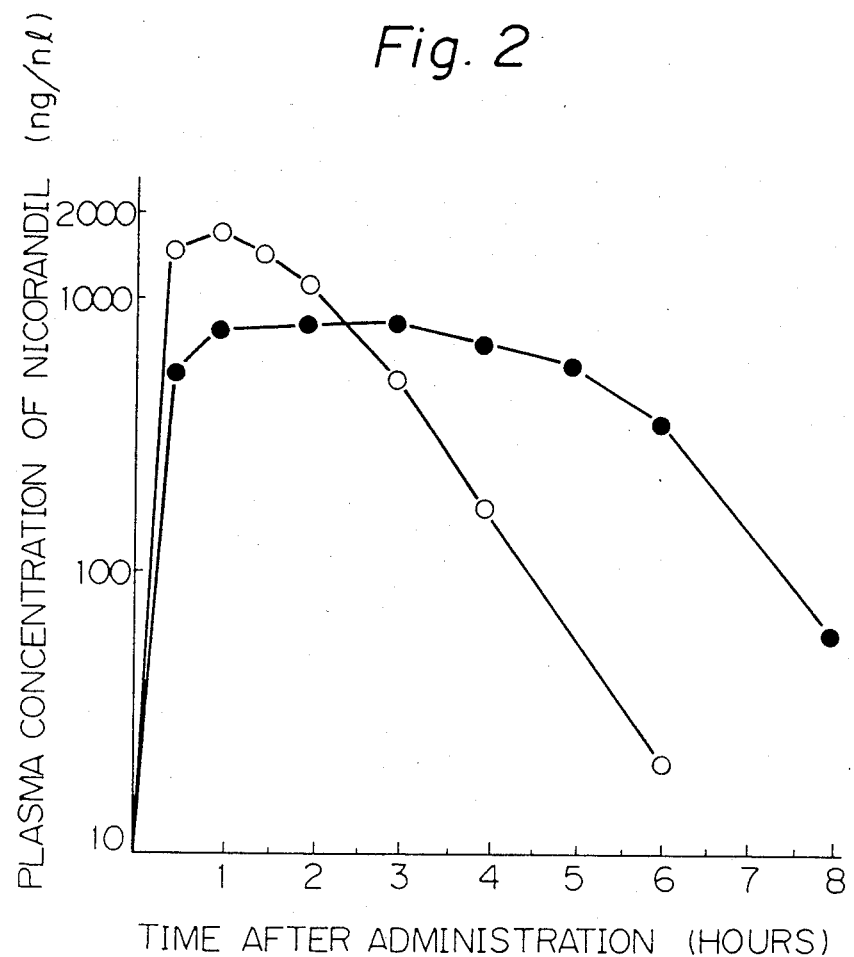
FIG. 2 is a graph showing the change of nicorandil level in plasma of beagle dogs with respect to the multi-layer layer tablet gradually releasing nicorandil prepared in Example 10 (—•—), and the ordinary tablet of the Comparative Example (—•—).

The dissolution profiles of these tablets are shown in FIGS. 1 and 2.

FIG. 1 shows the resutls of dissolution test carried out in a 500 ml of distilled water by the method defined in Japanese Pharmacopoeia, 10th Edition, Dissolution Test-Method 1 (the rotary basket method) at a rotation of 100 rpm, with respect to the multi-layer and the ordinary tablets.

FIG. 2 shows the time course of the average level of nicorandil concentration in plasma when the multi-layer or the ordinary tablet was orally administered in six beagle dogs.

EXAMPLE 11

| Nicorandil | 10 (mg) |
| --- | --- |
| Fumaric acid | 139.3 |
| Magnesium stearate | 0.7 |
| Total | 150.0 (mg) |

Nicorandil (10 g), fumaric acid (139.3 g) and magnesium stearate (0.7 g) were mixed in a polyethylene bag. The mixed powder was compressed by a single-punch tablet machine equipped with 8 mm$\phi$ flat-faced punches at 1.2 tons to make tablets each weighing 150 mg.

The dissolution test was carried out as in Example 10, and the results are shown in FIG. 1 as well as the resutls of Example 10.

What is claimed is:

1. A stable pharmaceutical composition comprising a therapeutic amount of nicorandil in admixture with a pharmaceutically acceptable and excipiently effective amount of a jet-milled sugar having an average particle size of about 3–10 microns selected from the group consisting of mannitol, lactose, sucrose, glucose, galactose, maltose and fructose.

2. A stable pharmaceutical composition comprising a therapeutic amount of nicorandil in admixture with an amount of powder organic acid effective to stabilize said pharmaceutical preparation to humidity, said organic acid being selected from the group consisting of fumaric acid, oxalic acid, salicylic acid, tartaric acid and glutaric acid.

3. The composition of claim 2, wherein said organic acid is present in an amount of no less 0.1% by weight based on the total weight of the preparation.

4. The composition of claim 3, wherein said organic acid is present in an amount no greater than about 95% by weight based on the total weight of the composition.

5. The composition of claim 3, wherein said organic acid is fumaric acid.

* * * * *